United States Patent
Ebinuma et al.

(10) Patent No.: US 6,541,215 B1
(45) Date of Patent: Apr. 1, 2003

(54) QUANTITATIVE DETERMINATION METHOD OF MANNOSE AND REAGENT THEREFOR

(75) Inventors: Hiroyuki Ebinuma, Ryugasaki (JP); Koji Ushizawa, Ryugasaki (JP)

(73) Assignee: Daiichi Pure Chemicals Co., Ltd., Tokyo (JP)

( * ) Notice: Subject to any disclaimer, the term of this patent is extended or adjusted under 35 U.S.C. 154(b) by 83 days.

(21) Appl. No.: 09/708,454

(22) Filed: Nov. 9, 2000

(30) Foreign Application Priority Data

Nov. 10, 1999 (JP) .......................... 11-319569
May 17, 2000 (JP) ...................... 2000-144414

(51) Int. Cl.$^7$ .......................... C12Q 1/26; C12Q 1/54; C12Q 1/32
(52) U.S. Cl. .......................... 435/25; 435/14; 435/823; 435/26; 435/962
(58) Field of Search .......................... 435/25, 14, 823, 435/26, 962

(56) References Cited

U.S. PATENT DOCUMENTS 4,734,366 A * 3/1988 Arena et al. ................ 435/105
5,942,424 A * 8/1999 Woodward et al. ......... 435/168

FOREIGN PATENT DOCUMENTS

JP 63-248397 10/1998
JP 11-266896 10/1999

OTHER PUBLICATIONS

Elja Pitkänen, "Mannose, mannitol, fructose and 1,5–anhydroglucitol concentrations measured by gas chromatography/mass spectrometry in blood plasma of diabetic patients," Clinca Chimica Aca (1996), pp. 91–103.

Louis De Repentigny, et al., "Comparison of Enzyme Inmmunoassay and Gas–Liquid Chromatography for the Rapid Diagnosis of Invasive Candidiasis in Cancer Patients," Journal of Clinical Microbiology, Jun. 1985, vol. 21, No. 6, pp. 972–979.

Thomas P. Monson, et al., "D–Mannose in Human Serum, Measured as Its Aldononitrile Acetate Derivative," Clinical Chemistry, vol. 25, No. 8, 1979, pp. 1384–1387.

(List continued on next page.)

*Primary Examiner*—Louise N. Leary
(74) *Attorney, Agent, or Firm*—Smith, Gambrell & Russell, LLP

(57) ABSTRACT

Disclosed are a method for quantitatively determining mannose, which comprises reacting mannose in a specimen with an enzyme which is capable of oxidizing the mannose by dehydrogenation, in the presence of an electron acceptor, and quantitatively determining a formed reductant of the electron acceptor; and a reagent for the quantitative determination of mannose.

13 Claims, 3 Drawing Sheets

OTHER PUBLICATIONS

Seiichi Toyota, et al., "Anti–Bacterial Defense Mechanism of the Urinary Bladder Role of Mannose in Urine," Bulletin of Japan Urology Association, 80, 1989, pp. 1816–1823.

Kokichi Soyama, "Enzymatic Determination of D–Mannose in Serum," Clinical Chemistry, vol. 30, No. 2, 1984, pp. 293–294.

Elja Pitkänen, "Enzymatic Determination of Unbound D–Mannose in Serum," Eur. J. Clin Chem. Clin. Biochem 1997, 35(10), pp. 761–766.

Koji Okamoto, "Enzymatic Studies on the Formation of 5–Ketogluconic Acid by Acetobacter suboxydans," The Journal of Biochemistry, vol. 53, No. 5, 1963, pp. 348–353.

Gad Avigad, et al., "Purification and Properties of a Nicotinamide Adenine Dinucleotide Phosphate–linked Aldohexose Dehydrogenase from Gluconobacter cerinus," The Journal of Biological Chemistry, vol. 243, No. 8, Apr. 25, 1968, pp. 1936–1941.

A. Stephens Dahms, et al., "D–Fucose Metabolism in a Pseudomonad," The Journal of Biological Chemistry, vol. 247, No. 7, Apr. 10, 1972, pp. 2222–2227.

Elja Pitkänen, et al., "Enzymatic Determination of Unbound D–Mannose in Serum," Eur. J. Clin. Chem Clin Biochem, vol. 35, No. 10, pp. 761–766.

Copy of European Search Report for counterpart application no. EP 00309379.6, dated Feb. 16, 2001.

Institute for Fermentation, Osaka (IFO), List of Cultures, Microorganisms $10^{th}$ Edition, 1996, pp. v–vi and pp. 151–152.

* cited by examiner

QUANTITATIVE DETERMINATION METHOD OF MANNOSE AND REAGENT THEREFOR

BACKGROUND OF THE INVENTION

The present invention relates to an accurate and convenient quantitative determination method of mannose by an enzyme method and a reagent for the quantitative determination.

Mannose which is a type of a hexose, exists in human blood in a slight amount. As the route of supply, it has been known that mannose is supplied mainly by a glucose metabolic system, not by ingestion of foods. The concentration of mannose in blood is usually as slight as about 0.5 mg/dl. However, it is known that the concentration tends to be high in the cases of patients suffering from diabetes who lacks the ability of controlling the blood sugar (Clinica. Chimica Acta 251; 1996 pp91–103) or fungal infection (J. Clin. Microbiol. 21(6); 1985 pp972–979), and it has been suggested that the mannose concentration is useful for diagnosis of these diseases.

As a method for measuring mannose, gas chromatography method (Clin. Chem 25; 1979; pp1384–1387), liquid chromatography method (Bulletin of Japan Urology Association, 80; 1989; pp1816–1823), enzyme method (Clin. Chem 30(2); 1984 pp293–294) and the like are known.

For example, in the enzyme method, since it is hard to conduct accurate quantitative determination if a specimen or sample contains glucose, it is necessary to eliminate the glucose. In the method of Soyama et al (Clin. Chem 30; 1984 pp293–294), glucose in the specimen is preliminarily eliminated by using glucose oxidase and catalase. Then, in the presence of adenosine triphosphate (hereinafter referred to as ATP), mannose is reacted with hexokinase to convert it to mannose 6-phosphate, and then reacted with mannose 6-phosphate isomerase to convert it to fructose 6-phosphate, and further reacted with glucose 6-phosphate isomerase to convert it to glucose 6-phosphate, and at the last, in the presence of oxidative nicotinamide adenine dinucleotide as a coenzyme (hereinafter referred to as NAD), reacted with glucose 6-phosphate dehydrogenase, and then the absorbance (340 nm) of the formed reductive nicotinamide adenine dinucleotide (hereinafter referred to as NADH) is measured by a spectrophotometer to quantitatively determine the mannose.

Further, as an improvement of the above enzyme method, a method for quantitatively determining mannose is reported by Pitkanen et al (Eur. J. Clin. Chem. Clin. Biochem 35(10); 1997 pp761–766), wherein hexokinase and glucose 6-phosphate isomerase are reacted to a specimen wherein glucose and fructose co-exist in the presence of ATP and an oxidative nicotinamide adenine dinucleotide phosphate (hereinafter referred to as NADP), thereby converting the glucose and fructose to glucose 6-phosphate; glucose 6-phosphate dehydrogenase is further added thereto to convert the glucose 6-phosphate to gluconolacton 6-phosphate; the formed reductive nicotinamide adenine dinucleotide phosphate (hereinafter referred to as NADPH) is degraded under acidic condition with hydrochloric acid in order to eliminate the influence of glucose and the like; and then in the same manner as above, in the presence of ATP and NADP, mannose is reacted with hexokinase, mannose 6-phosphate isomerase, glucose 6-phosphate isomerase and glucose 6-phosphate dehydrogenase, and the absorbance (340 nm) of the formed NADPH is measured.

However, in the above-mentioned enzyme methods, since it is required to conduct a complicated enzyme conjugated system wherein various enzymatic reactions are combined, it is difficult to optimize the conditions of all enzymes. Further, since various expensive enzymes are combined for use, there is a problem in the aspect of costs. Furthermore, there is a drawback that these methods are susceptible to influences of components derived from biological specimens or impurities.

On the other hand, in the gas chromatography method and liquid chromatography method, since it is necessary to conduct cumbersome operations such as derivation or labeling of e.g. fluorescence, and to use special apparatuses, these methods are not suitable for treatment of many specimens.

SUMMARY OF THE INVENTION

It is an object of the present invention to provide a method for quantitatively determining mannose and a reagent for quantitative determination, by which it becomes possible to conduct treatment of many specimens accurately and conveniently.

In order to accomplish the above object, in one aspect, the present invention provides method for quantitatively determining mannose, which comprises reacting mannose in a specimen with an enzyme which is capable of oxidizing the mannose by dehydrogenation, in the presence of an electron acceptor, and quantitatively determining a formed reductant of the electron acceptor.

In the above method, when the specimen contains glucose in addition to the mannose, it is preferred that, before the reaction with the enzyme, the glucose in the specimen is converted by a glucose eliminator into a structure that is not reactive with the enzyme.

In the above method, the enzyme is preferably a glucose dehydrogenase which belongs to an enzyme number EC class 1.1.1.119, more preferably a aldohexose dehydrogenase which is derived from a microorganism belonging to a gluconobacter genus. As the specimen, it is preferred that the specimen is at least one biological specimen selected from the group consisting of blood, serum, plasma, cerebrospinal fluid and urine, or a specimen prepared from said biological specimen.

In another aspect, the present invention provides a reagent for quantitative determination of mannose, which comprises an enzyme which is capable of oxidizing mannose by dehydrogenation in the presence of an electron acceptor, and an electron acceptor useful for the enzyme.

The reagent preferably further contains a glucose eliminator. Furthermore, the enzyme is preferably a glucose dehydrogenase which belongs to an enzyme number EC class 1.1.1.119, more preferably an aldohexose dehydrogenase which is derived from a microorganism belonging to a gluconobacter genus. Moreover, the glucose eliminator preferably contains a glucose 6-position phosphorylating enzyme, and adenosine triphosphate. Further, the electron acceptor is NADP as a coenzyme.

According to the present invention, since an enzyme which reacts directly with mannose and is capable of oxidizing mannose by dehydrogenation, is used without conducting the measurement through the complicated enzyme conjugated system, it is possible to quantitatively determine mannose conveniently and conduct treatment of many specimens. Further, when the glucose eliminator is used, since the measurement is hardly influenced by the glucose in the specimen, it is possible to quantitatively determine mannose accurately.

DETAILED DESCRIPTION OF THE INVENTION

Figure 1:
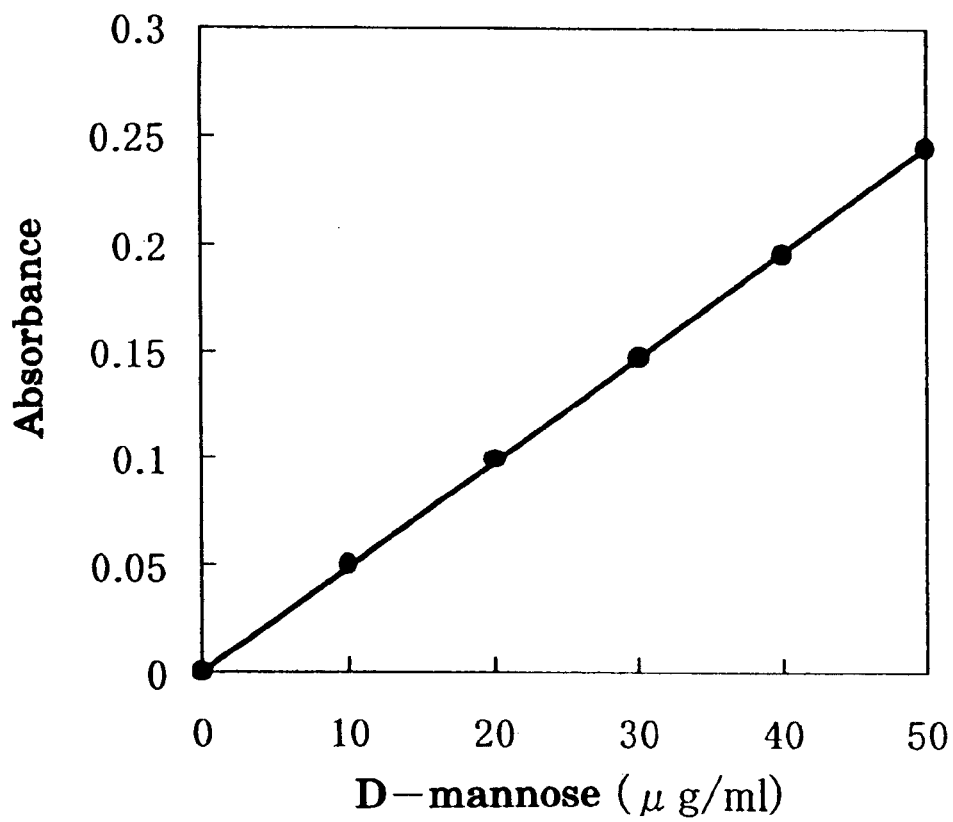
FIG. 1 is a graph showing the results of measurement of mannose solutions of various concentrations by using a first reagent containing an electron acceptor and a second reagent containing aldohexose dehydrogenase.

In the present invention, as the specimen (test specimen), there is no particular limitation as far as it is intended to measure the concentration of mannose. However, it is preferred to use a biological specimen such as blood, serum, plasma, cerebrospinal fluid and urine, or a specimen prepared from these biological specimens, for example, a specimen pre-treated by various methods so that mannose can easily be measured, etc. As such pretreatment, for example, a treatment wherein glucose is preliminarily removed or eliminated from a specimen in which the glucose co-exists.

As the enzyme used in the present invention, there is no particular limitation as far as it is an enzyme which is capable of oxidizing mannose by dehydrogenation, in the presence of an electron acceptor (hereinafter referred to as "mannose dehydrogenase"). However, preferably, an enzyme which belongs to an enzyme number EC class 1.1.1.119 may be mentioned. Specifically, for example, NADP-dependent glucose dehydrogenase obtainable from Acetobacter suboxydans described in OKAMOTO's document (J. Biochem. 53(5) 1963 pp348–353), and NADP-dependent aldohexose dehydrogenase obtainable from *Gluconobacter cerinus* described in AVIGAD et al's document (J. Biol. Chem. 243(8) 1968 pp1936–1941), NAD-dependent aldohexose dehydrogenase described in DAHMS et al's document (J. Biol Chem. 247(7) 1972 pp2222–2227), may be mentioned.

The above enzyme is particularly aldohexose dehydrogenase derived from a microorganism belonging to gluconobacter genus. As the microorganism belonging to gluconobacter genus, for example, *Gluconobacter asaii* (*G. assai*) IFO 3276, Gluconobacter cerinus (*G. cerinus*) IFO 3267, *Gluconobacter frateurii* (*G. frateurii*) IFO 3264, and *Gluconobacter oxydans* (*G. oxydans*) IFO 14819, may be mentioned. The enzyme can be obtained by culturing such microorganism and recovering the cells, and then destroying the cells by ultrasonic wave treatment or the like, and the formed destroyed solution is, if necessary, purified by combining column chromatographys such as ammonium sulfate fractionation, ion exchange chromatography, hydrophobic chromatography, hydroxyapatite gel and gel filtration.

The concentration of the mannose dehydrogenase in use is not particularly limited, but preferably from 0.1 to 100 units/liter, more preferably from 1 to 10 units/liter.

In the present invention, as the electron acceptor, one or two or more of coenzymes such as NAD and NADP, oxygen, phenazine methosulfate, dichlorophenol indophenol, ferricyanide compounds, tetrazolium salts may appropriately be selected for use. Particularly preferred is coenzyme NADP. The concentration of the electron acceptor in use is preferably from 0.1 to 10 mmolliter, particularly preferably from 0.5 to 2 mmol/liter.

Further, in order to quantitatively determine the reductant of the electron acceptor, a color producing reagent which develops color by the reduction of the electron acceptor. The color producing reagent may be appropriately selected depending upon the electron acceptor to be used. For example, in order to quantitatively determine NADPH as the reductant of coenzyme NADP, a method may be mentioned wherein a tetrazolium salt is allowed to coexist together with phenazine methosulfate or diaphorase, and the formed formazan dye is subjected to colorimetric quantitative determination.

Furthermore, since the mannose dehydrogenase used in the present invention shows action against not only mannose but also glucose, it is likely to receive the influence of glucose particularly when the mannose in the biological specimens such as serum or plasma is to be measured. Accordingly, in order to increase the measurement precision to the biological specimen, it is preferred to use a glucose eliminator together. As the glucose eliminator, it is preferred to use the one containing ATP and a glucose 6-position phosphorylating enzyme.

As the glucose 6-position phosphorylating enzyme, glucokinase, hexokinase may be mentioned. There is no particular limitation as far as it belongs to EC 2.7.1.2. or EC 2.7.1.1, and commercially available ones can be used. However, glucokinase which has a high specificity to glucose may preferably be used. The amount thereof depends on the glucose amount in the specimen, but is generally from 0.1 to 50 u/ml. Further, the ATP amount necessary for the phosphorylation of glucose depends on the glucose amount in the specimen, but is generally from 1 to 20 mM. Moreover, as the one accelerating the glucose phosphorylation, in general, magnesium ions of e.g. an inorganic or organic salt is contained in an amount of from about 5 to 50 mM. The glucose phosphorylation for the elimination of glucose is conducted at 20 to 50° C., preferably 25 to 37° C. for about 10 minutes immediately after the addition in a buffer solution of pH 6 to 10.

As the buffer solution useful for the present invention, generally usable ones of pH 6 to 10 such as a phosphate buffer solution, glycine buffer solution, tris-hydrochloric acid buffer solution, Good's buffer solution and boric acid buffer solutin, may be used.

As the reagent for quantitative determination of mannose of the present invention, the glucose eliminator and the reagent for quantitative determination may be separately prepared and combined for use. More specifically, it may preferably be composed of two reagents i.e. a first reagent containing the electron acceptor and the glucose eliminator, and a second reagent containing the mannose dehydrogenase.

The reagent for quantitative determination of mannose is added to a biological specimen for reaction, and then the electron acceptor reduced in the reaction solution is measured by, for example, measuring the absorbance at the absorption wavelength specific to the reductant of the electron acceptor, or measuring the color development intensity of the color producing reagent which develops color by the reduction of the electron acceptor.

Hereinbelow, the present invention will be described specifically with reference to examples. However, it should be mentioned that the present invention is by no means limited thereto.

Preparation Example of enzyme (preparation of aldohexose dehydrogenase derived from *gluconobacter asaii*)

*Gluconobacter asaii* (IFO 3276) was inoculated on a medium containing 0.5% yeast extract and 1% of fructose, and shake cultured at 28° C. for 24 hours, followed by centrifugal separation to obtain cells. The cells were suspended in a 20 mM phosphate buffer solution (pH7) and treated with an ultrasonic oscillator under ice-cooling, and then the broken solution was subjected to centrifugal separation to remove the cell residues and obtain a crude enzyme solution.

Ammonium sulfate powder was added to this crude enzyme solution and dissolved therein so that the ammonium sulfate amount would be 30% of saturation. The precipitated proteins were removed by centrifugal separation. The obtained supernatant was allowed to pass through a Butyl Toyopearl column to adsorb enzymes thereon, and then the enzymes were eluted in a linear gradient with a 20 mM phosphate buffer solution (pH7) containing ammonium sulfate in an amount of 30% to 0% of saturation.

The enzymatic activities of respective elute fractions were measured and active fractions were recovered. The active fractions were dialyzed with a 20 mM phosphate buffer solution (pH7) for desalting, and then this was allowed to pass through a DEAE Toyopearl column to adsorb enzymes thereon, and the enzymes were eluted in a linear gradient with a 20 mM phosphate buffer solution (pH7) containing 0 to 0.25M of NaCl.

The enzymatic activities of respective elute fractions were measured and active fractions were recovered. The active fractions were dialyzed with a 20 mM phosphate buffer solution (pH7) for desalting, and then this was allowed to pass through a hydroxyapatite column to adsorb enzymes thereon, and the enzymes were eluted in a linear gradient with a 20 to 150 mM phosphate buffer solution (pH7). The enzymatic activities of respective elute fractions were measured and active fractions were recovered, and this was referred to as purified enzyme solution.

EXAMPLE 1

Using the aldohexose dehydrogenase obtained in the above Preparation Example of enzyme and a coenzyme NADP as an electron acceptor, a reagent for quantitative determination comprising a first reagent and a second reagent as indicated below, was prepared.

First Reagent (pH 8.5):
  125 mM tris-hydrochloric acid buffer solution
  1.25 mM NADP
  0.75 mM WST-1 (tradenade, manufactured by K.K. Dojin Kagaku Kenkyusho)
  1.25% Tween 20 (Polyoxyethylene (20) sorbitan monolaurate) 6.25 u/ml Diaphorase Second Reagent (pH 7.0):
  20 mM Phosphate buffer solution
  23 u/ml Aldohexose dehydrogenase Using this reagent, mannose solutions of various concentrations (0 to 50 µg/ml) were measured as indicated below.

To 8 µl of each of mannose solutions of various concentrations, 256 µl of the first reagent was added and reaction was carried out at 37° C. for 5 minutes, and then 56 µl of the second reagent was added and likewise reaction was carried out at 37° C. for 5 minutes. Then, the absorbance was measured by two points assay with a main wavelength of 450 nm and a sub wavelength of 700 nm. These operations were conducted with a Hitachi 7150 model automatic analyzer. The results are shown in FIG. 1.

From FIG. 1, it was found that a linear luminous absorbance was obtained with the mannose concentration of from 0 to 50 µg/ml and it is possible to conduct accurate quantitative determination of mannose in a low concentration range.

EXAMPLE 2

Quantitative Determination of Mannose by a Reagent System in Which a Glucose Eliminator is Contained in Combination, Using the aldohexose dehydrogenase obtained in the above Preparation Example of enzyme, a coenzyme NADP as an electron acceptor and glucokinase and ATP as glucose eliminators, a reagent for quantitative determination of mannose comprising a first reagent and a second reagent as indicated below, was prepared.

First Reagent (pH8.5):
  125 mM tris-hydrochloric acid buffer solution
  1.25 mM NADP
  0.75 mM WST-1 (tradenade, manufactured by K.K. Dojin Kagaku Kenkyusho)
  1.25% Tween 20 (Polyoxyethylene (20) sorbitan monolaurate)
  6.25 u/ml Diaphorase
  12.5 u/ml Glucokinase
  10 mM ATP
  2 mM Magnesium acetate Second Reagent (pH 7.0):
  20 mM Phosphate buffer solution
  23 u/ml Aldohexose dehydrogenase At first, likewise in Example 1, this reagent was reacted with each of mannose solutions of various concentrations (0 to 50 µg/ml), and the absorbances of the reaction solutions were measured. The results are shown in FIG. 2.

Then, the above reagent was reacted with each of solutions containing mannose of a constant concentration (about 10 µg/ml) and glucose of various concentrations (0 to 1,000 mg/dl), and the absorbances of the reaction solutions were measured. The results are shown in FIG. 3.

Figure 2:
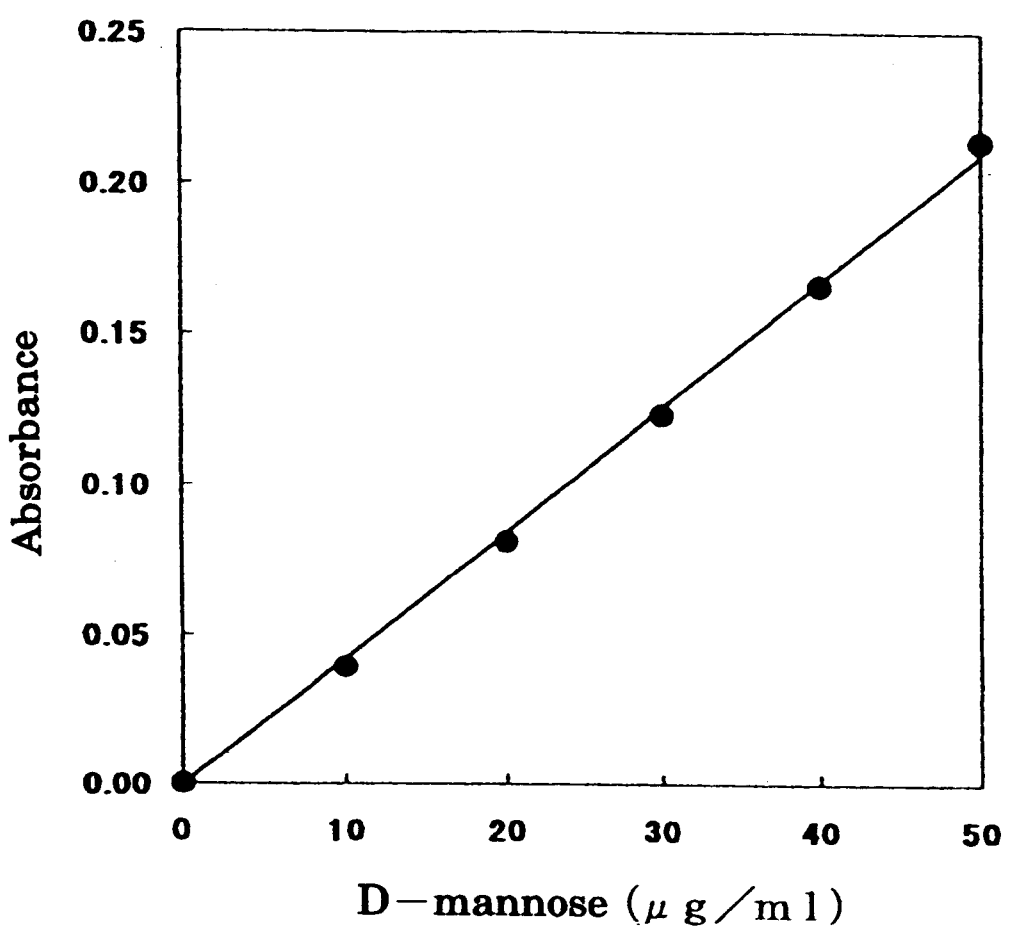
FIG. 2 is a graph showing the results of measurement of mannose solutions of various concentrations by using a first reagent containing an electron acceptor and a glucose eliminator, and a second reagent containing aldohexose dehydrogenase.

From FIG. 2, it was found that a linear luminous absorbance was obtained with the mannose concentration of from 0 to 50 µg/ml and it is possible to conduct accurate quantitative determination of mannose even in a reagent system wherein a glucose eliminator is used in combination.

Figure 3:
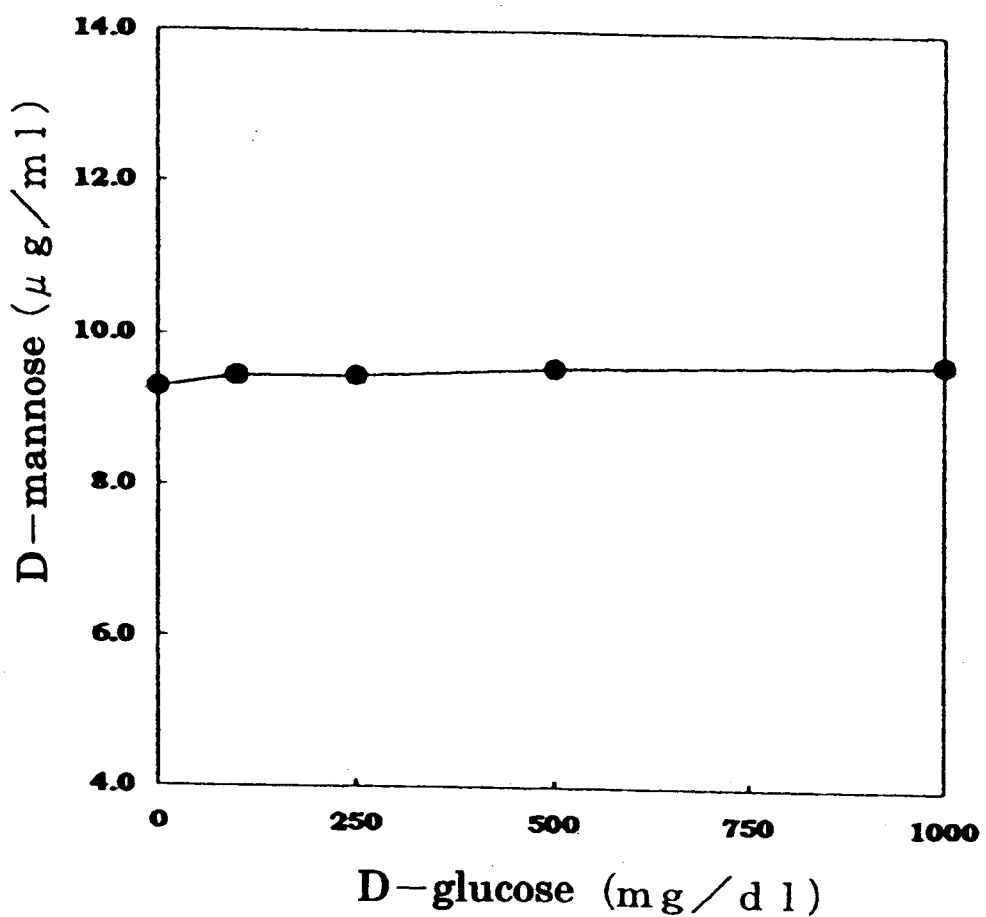
FIG. 3 is a graph showing the results of measurement of solutions containing mannose of a constant concentration and glucose of varied concentrations by using a first reagent containing an electron acceptor and a glucose eliminator, and a second reagent containing aldohexose dehydrogenase.

Further, from FIG. 3, it was found that even if the glucose concentration in the specimen varies from 0 to 1,000 mg/dl, a constant absorbance depending upon the mannose concentration can be obtained. From this result, it is evident that even in a specimen containing glucose in a high concentration, the mannose in the specimen can be quantitatively determined accurately.

EXAMPLE 3

Mannose was measured using the reagent of Example 2, with respect to specimens prepared by adding a 100 µg/ml mannose aqueous solution at a ratio of 1 part by volume to 9 parts by volume of each of five types of serums (Serum Nos. 1 to 5), and as a control, specimens to which purified water was added instead of the mannose aqueous solution. Using the measured values and a calibration curve (FIG. 2) obtained in Example 2, the mannose amounts were quantitatively determined, and the recoveries of the added mannose stoichiometric amounts were obtained. The results are indicated in Table 1.

TABLE 1

| Serum No. | Mannose aqueous solution added (A) (µg/ml) | Purified water added (B) (µg/ml) | A − B (µg/ml) |
|---|---|---|---|
| 1 | 15.4 | 5.6 | 9.8 |
| 2 | 15.4 | 6.1 | 9.2 |
| 3 | 16.9 | 7.3 | 9.6 |
| 4 | 19.5 | 9.9 | 9.6 |
| 5 | 13.9 | 4.4 | 9.5 |

From the results of FIG. 1, it is found that the recovery is excellent to the added mannose stoichiometric amount (10 µg/ml) and it is possible to conduct accurate quantitative determination of mannose in the serum.

As mentioned above, according to the present invention, an electron acceptor is added to a specimen containing mannose and a mannose dehydrogenase is reacted thereto, whereby the mannose dehydrogenase directly reacts with the mannose to oxidize the mannose and at the same time, directly reduce the electron acceptor, and accordingly, by measuring the formed reductant of the electron acceptor, accurate quantitative determination of mannose can be made with a high sensitivity. Further, since the reaction system is simple, the present invention can be easily applied to various automatic analyzer and is suitable for the treatment of many specimens.

Moreover, by using a glucose eliminator in combination to reduce the glucose coexisting in the specimen, the specimen becomes to a level such that the influence of glucose can be substantially ignored, whereby even in biological specimens such as serum or plasma, a high measurement precision can be obtained by a simple operation.

What is claimed is:

1. A method for quantitatively determining mannose in a specimen containing mannose, which comprises:
   adding to the specimen containing mannose an enzyme which is capable of oxidizing the mannose by dehydrogenation in the presence of an electron acceptor, and an electron acceptor for the enzyme,
   passing a hydrogen atom of the mannose contained in the specimen to the electron acceptor by the action of the enzyme, so as to oxidize the mannose and reduce the electron acceptor, and
   quantitatively determining a formed reductant of the electron acceptor, wherein the presence of said formed reductant indicates that mannose is present in the specimen, further wherein the amount of said formed reductant is proportional to the amount of mannose present in the specimen.

2. The method according to claim 1, wherein the specimen contains glucose in addition to the mannose, and before the reaction with the enzyme, the glucose in the specimen is converted by a glucose eliminator into a structure that is not reactive with the enzyme.

3. The method according to claim 1, wherein the enzyme is a glucose dehydrogenase which belongs to an enzyme number EC class 1.1.1.119.

4. The method according to claim 1, wherein the enzyme is an aldohexose dehydrogenase which is derived from a microorganism belonging to a gluconobacter genus.

5. A method for quantitatively determining mannose in a specimen containing mannose, which comprises:
   adding to the specimen containing mannose an enzyme which is capable of oxidizing the mannose by dehydrogenation in the presence of an electron acceptor, and an electron acceptor for the enzyme,
   passing a hydrogen atom of the mannose contained in the specimen to the electron acceptor by the action of the enzyme, so as to oxidize the mannose and reduce the electron acceptor, and
   quantitatively determining a formed reductant of the electron acceptor, wherein the presence of said formed reductant indicates that mannose is present in the specimen, further wherein the amount of said formed reductant is proportional to the amount of mannose present in the specimen;
   wherein the specimen contains glucose in addition to the mannose, and before the reaction with the enzyme, the glucose in the specimen is converted by a glucose eliminator into a structure that is not reactive with the enzyme, wherein the glucose eliminator contains a glucose 6-position phosphorylating enzyme, and adenosine triphosphate.

6. The method according to claim 1, wherein the electron acceptor is an oxidative nicotinamide adenine dinucleotide phosphate as a coenzyme.

7. The method according to claim 1, wherein the specimen is at least one biological specimen selected from the group consisting of blood, serum, plasma, cerebrospinal fluid and urine, or a specimen prepared from said biological specimen.

8. A reagent for quantitative determination of mannose in a specimen containing mannose, which comprises an enzyme which is capable of oxidizing mannose by dehydrogenation in the presence of an electron acceptor, and an electron acceptor for the enzyme.

9. The reagent according to claim 8, which further comprises a glucose eliminator.

10. The reagent according to claim 8, wherein the enzyme is a glucose dehydrogenase which belongs to an enzyme number EC class 1.1.1.119.

11. The reagent according to claim 8, wherein the enzyme is an aldohexose dehydrogenase which is derived from a microorganism belonging to a gluconobacter genus.

12. A reagent for quantitative determination of mannose in a specimen containing mannose, which comprises an enzyme which is capable of oxidizing mannose by dehydrogenation in the presence of an electron acceptor, and an electron acceptor for the enzyme, the reagent further comprising a glucose eliminator, wherein the glucose eliminator contains a glucose 6-position phosphorylating enzyme, and adenosine triphosphate.

13. The reagent according to claim 8, wherein the electron acceptor is an oxidative nicotinamide adenine dinucleotide phosphate as a coenzyme.

* * * * *